United States Patent
Boston et al.

(10) Patent No.: US 6,297,626 B1
(45) Date of Patent: Oct. 2, 2001

(54) FLUID PARTICLE SENSOR APPARATUS AND METHOD FOR DETECTING FERROUS AND NON-FERROUS METALS

(75) Inventors: Timothy A. Boston, Tremont; John W. Crayton, Peoria; Lisa A. Creger, Metamora, all of IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 09/221,927

(22) Filed: Dec. 28, 1998

(51) Int. Cl.$^7$ .............................. G01N 27/74; G01R 33/12
(52) U.S. Cl. ..................... 324/204; 73/61.42; 340/631
(58) Field of Search .................................. 324/204, 234, 324/236; 73/61.42; 340/631

(56) References Cited

U.S. PATENT DOCUMENTS

| | | | |
|---|---|---|---|
| 4,219,805 | 8/1980 | Magee et al. | 340/631 |
| 4,416,771 | * 11/1983 | Henriques . | |
| 5,502,378 | 3/1996 | Atteberry et al. | 324/204 |
| 5,608,315 | 3/1997 | Crayton et al. | 324/204 |
| 5,708,198 | * 1/1998 | Fitch et al. | 73/61.42 |

* cited by examiner

Primary Examiner—Gerard R. Strecker

(74) Attorney, Agent, or Firm—Haverstock, Garrett & Roberts

(57) ABSTRACT

A sensor apparatus for detecting both ferrous and non-ferrous particles in a fluid including a housing adapted for insertion into a fluid line, the housing having a collection cavity formed therewithin for trapping and holding metallic particles which are suspended in the fluid as the fluid passes through the sensor. A first coil wound below the collection cavity and a second coil wound about the collection cavity, the inductance of the first coil being responsive to the temperature of the fluid passing through the sensor and the inductance of the second coil being responsive to the ferrous and non-ferrous particle accumulation within the collection cavity. An electromagnetic coil is spaced above the second coil to attract ferrous particles away from the vicinity of the second coil. Based upon eddy current principles and because eddy currents are a function of material conductivity, a first energization of the second coil generates a signal indicative of the total ferrous and non-ferrous particle accumulation within the collection cavity and a second energization of the second coil with the electromagnetic coil likewise energized generates a signal indicative of just the non-ferrous particle accumulation within the collection cavity. A microprocessor coupled to the coils calculates the percentage of ferrous and non-ferrous particles in the collection cavity and outputs such information for diagnostic, prognostic and trend analysis purposes.

15 Claims, 3 Drawing Sheets

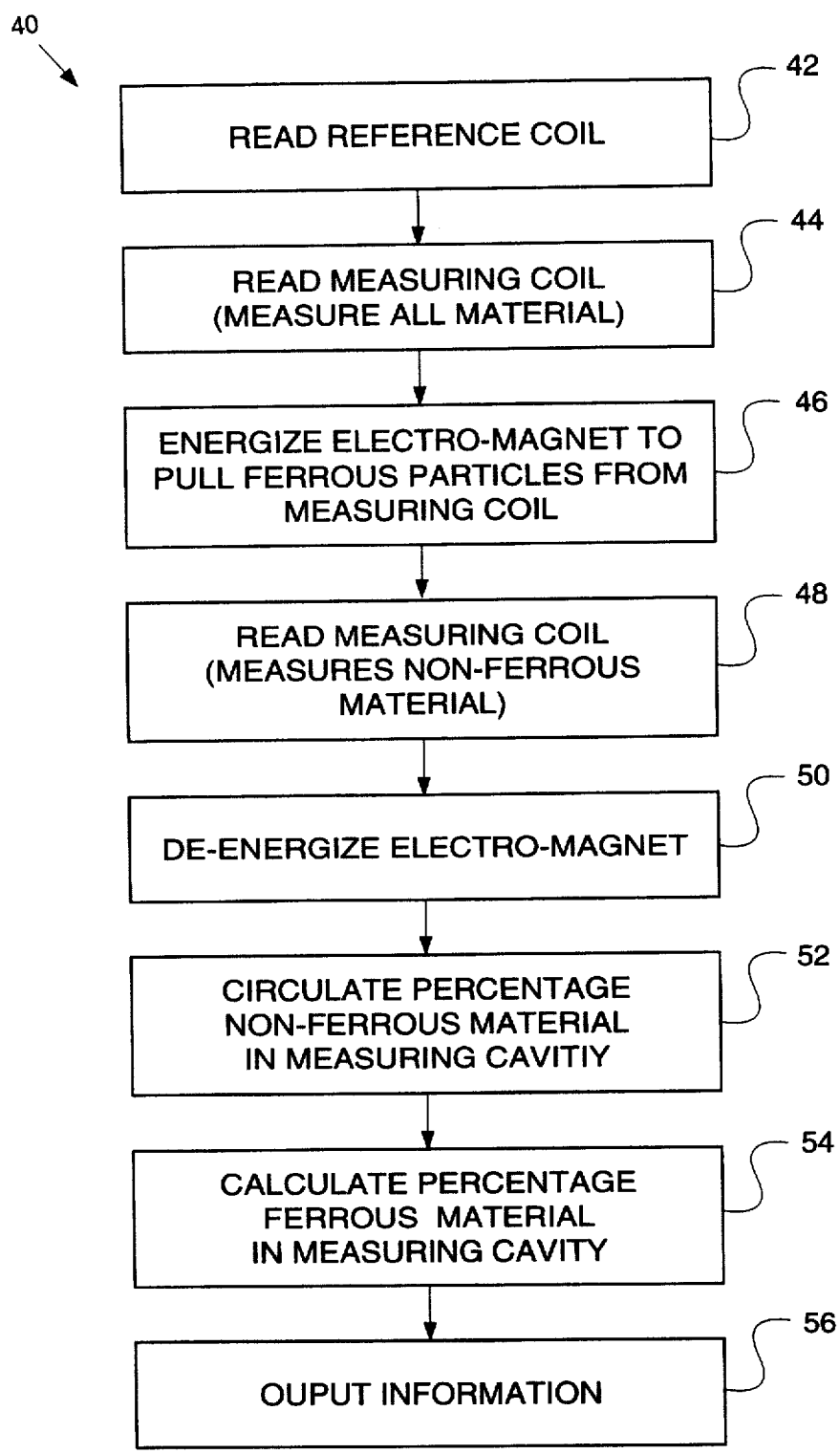

FLUID PARTICLE SENSOR APPARATUS AND METHOD FOR DETECTING FERROUS AND NON-FERROUS METALS

TECHNICAL FIELD

This invention relates generally to an apparatus for detecting particles in a fluid medium and, more particularly, to an apparatus and method for detecting ferrous and non-ferrous particles in a fluid medium.

BACKGROUND ART

Mechanical systems such as engines and transmissions utilize a lubricating oil or other fluid to dissipate heat within the system and to reduce wear on system components. However, due to the nature of the systems, wear does occur, resulting in the presence of small metallic particles in the oil or other lubricating fluid.

Due to the normal wear and the natural breakdown of the oil or other lubricating fluid, the lubricating fluid in such systems must be changed periodically. This is typically done on a time or usage basis, for example, every 90 days or 2000 hours of use. While small metal particles may result from normal wear, larger particles are usually an indication of abnormal wear or a more serious problem. For example, the resulting wear creates abnormal amounts of metal particles within the lubricant. Under normal maintenance procedures, the metal particles would be present in the lubricant for an extended period of time. If this condition is not identified and the appropriate repairs completed, more expensive repairs including the replacement of major system components may result.

Detection of metallic particles in hydraulic systems is equally important as hydraulic systems represent large expenses in the event of component failure. If failures are detected early, repair expenses can be minimized; however, if catastrophic failure occurs, the large amounts of particles caused by the failure can enter the hydraulic system and cause damage to many other components. Fortunately, any catastrophic failure of one of the components is often preceded by the gradual breakup of one or more components. If this breakup can be detected, corrective action can be taken before any further damage to surrounding components occurs.

In the past, there have been several different ways to detect metallic particles within a fluid. One such system is described in U.S. Pat. No. 4,219,805. This system captures ferrous particles that are contained in a fluid medium, and indicates the mass of any significant individual ferrous particles and the total mass of such particles that have accumulated over a predetermined time period. However, this system is limited to the detection of ferrous particles, e.g., iron, as opposed to non-ferrous particles, e.g., copper, brass, or non-magnetic stainless steel.

In U.S. Pat. No. 5,502,378 assigned to the assignee of the present application, a sensor is disclosed that detects particles within a fluid that is generally comprised of a housing defining a cavity and a magnet disposed adjacent to the cavity bottom to attract particles into the cavity. A first coil is wound about the surface of the cavity. The induction of the first coil is responsive to the particle accumulation within the cavity. A second coil is wound about the magnet. The induction of the second coil is responsive to the temperature of the fluid and is independent of the particle accumulation within the cavity. This sensor is unable to distinguish between ferrous and non-ferrous particles.

Still further, in U.S. Pat. No. 5,608,315 assigned to the assignee of the present application, a sensor is disclosed that detects both ferrous and non-ferrous particles, this particular sensor utilizing four separate coils. In this sensor configuration, a first coil is provided for responsiveness to both ferrous and non-ferrous particles, a second coil is provided for responsiveness to the accumulation of ferrous particles only, and yet a third coil is provided as a reference coil for temperature measurement. A fourth electromagnetic coil is provided to attract particles into the proximity of the second coil measuring the ferrous particles. All four coils are wrapped around a bobbin. This sensor construction is very complex because the bobbin is a special part that limits the application of the sensor to different machines and the use of four separate coils requires additional electronics for the sensing of the metallic particles.

It would therefore be desirable if there were provided a fluid particle sensor that would more reliably detect both ferrous and non-ferrous materials in a fluid medium; that would provide easier maintenance and installation; and that would be much simpler in overall design.

Accordingly, the present invention is directed to overcoming one or more of the problems as set forth above.

DISCLOSURE OF THE INVENTION

In one aspect of the present invention, a sensor for detecting particles in a fluid medium is generally comprised of a housing having a collection cavity therewithin, the housing being easily adaptable for connection to a fluid line of a particular work machine or other apparatus that is to be monitored. The housing is inserted into the fluid line by conventional means and includes a screen positioned and located therewithin to trap particles within the housing and thereafter to allow such particles to accumulate and collect at the bottom of the collection cavity. A first coil is wound about the housing adjacent the bottom of the cavity, the first coil being responsive to the temperature of the fluid medium and being independent of the particle accumulation within the collection cavity. A second measuring coil is wound about the housing spaced above the first coil. The induction of the second coil is responsive to both ferrous and non-ferrous particle accumulations within the collection cavity. An electromagnetic coil is spaced above the second coil to extract or pull all of the ferrous particles from the collection cavity in the area of the second coil. The sensor also includes a microprocessor which will first measure the particle accumulation of both ferrous and non-ferrous particles contained within the collection cavity and thereafter extract the ferrous particles from the vicinity of the measuring coil and measure only the non-ferrous particles contained within the collection cavity. The present sensor then calculates the percentage of ferrous particles contained within the collection cavity and the percentage of non-ferrous particles and outputs such information to a control module for trend or component failure analysis.

BRIEF DESCRIPTION OF THE DRAWINGS

FIG. 3 is a flow chart illustrating the method of operation of the present fluid particle sensor device.

BEST MODE FOR CARRYING OUT THE INVENTION

Figure 1:
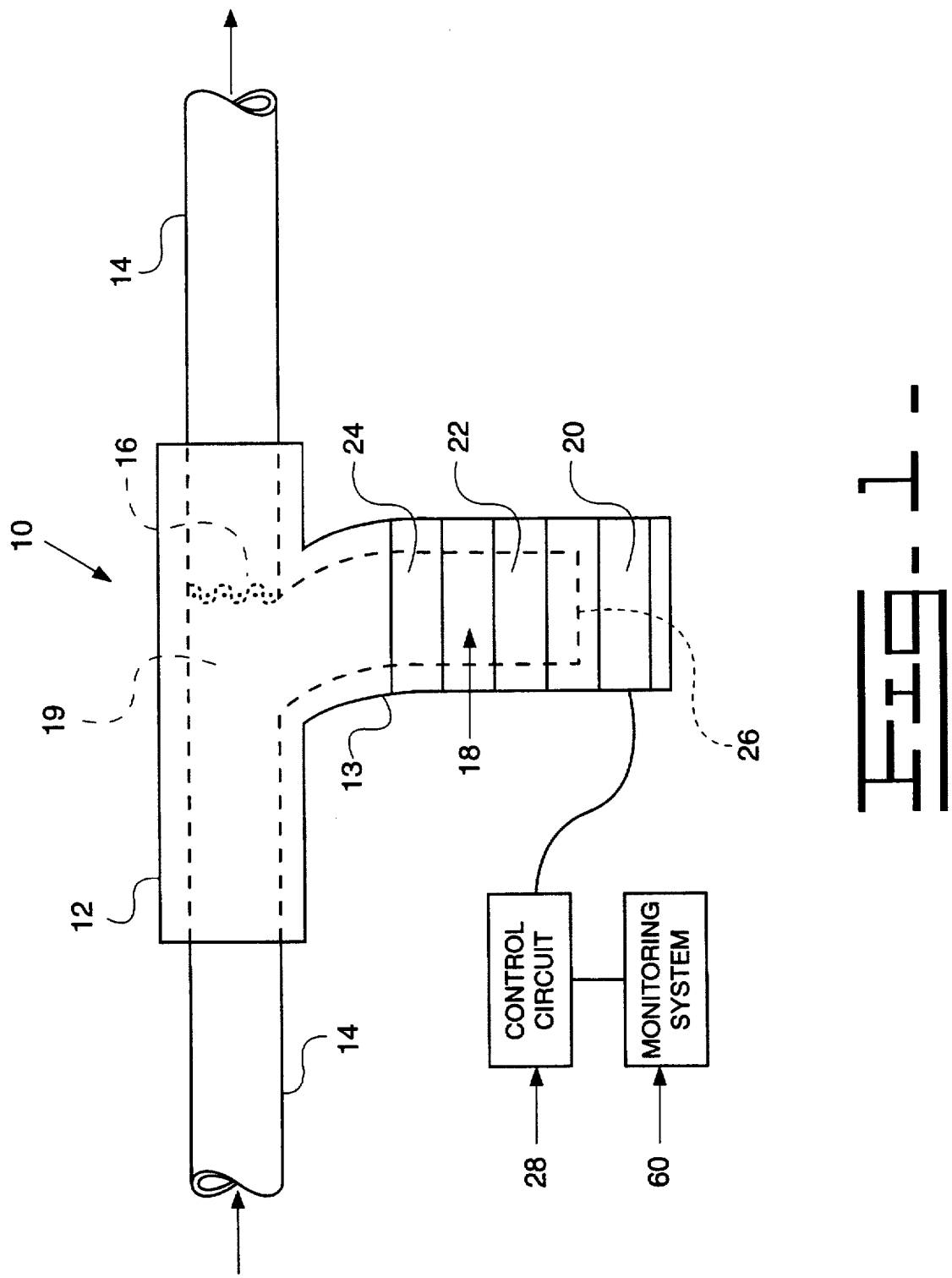
FIG. 1 is a partial, cutaway view of the sensor housing incorporating the principles of the present invention.

Referring to FIG. 1, there is shown a fluid particle sensing device 10 that incorporates the principles of the present invention. The device 10 filters metallic debris from a fluid and measures the quantity or accumulation of such metallic debris occurring in a particular fluid system, such as, an engine oil system, a hydraulic system, or a transmission system (not shown). The present sensor device 10 includes a housing portion 12 which is connected to a typical fluid line 14, the housing 12 being adapted for connection to the fluid line 14 in a conventional manner. The housing 12 is generally cylindrical in shape for easy mounting to the fluid line 14 and includes a screen 16 mounted therein to catch and trap particles in the fluid as such particles flow through the housing 12. The screen 16 is preferably disposed at substantially a right angle to the fluid line 14 as shown in FIG. 1, although the precise angular relationship of the screen 16 to the fluid line 14 is not critical so long as the metallic particles trapped against the screen 16 will fall and accumulate within the collection cavity 18. Collection cavity 18 is located in housing portion 13 which is angularly related to the housing portion 12 as shown in FIG. 1. The screen 16 is advantageously made of non-magnetic material and has a mesh size small enough to catch most particles while not significantly restricting flow. Fluid flows freely through the housing 12 and is filtered as it passes through the screen 16 and exits the housing 12 downstream as shown in FIG. 1.

As shown in FIG. 1, collection cavity 18 includes an inlet opening 19 located in housing portion 12 adjacent the lower portion of screen 16. The debris trapped by screen 16 is pulled downwardly into the cavity 18 by gravity and by the flow of fluid through housing 12. The cavity 18 does not extend all the way to the bottom of housing portion 13 as shown in FIG. 1. Wrapped around the bottom portion of housing 13 is a first reference coil 20. A second measuring coil 22 is wrapped around the housing 13 adjacent the bottom portion 26 of collection cavity 18, and an electromagnetic coil 24 is wrapped about the cavity 18 above the measuring coil 22. Particles in the fluid that are caught by the screen 16 fall into the cavity 18 and settle to the bottom at 26. This portion of collection cavity 18 will be used to measure the accumulation of both ferrous and non-ferrous particles in the fluid medium in a manner as will be hereinafter explained.

The first reference coil 20 located underneath the collection cavity 18 is provided to compensate for the changing temperature of the fluid. The inductance of the first coil 20 is therefore used as a baseline for determining the presence of particles within the cavity 18. The second coil 22 is generally wound in the form of a helix about the cavity 18 and is spaced above the first coil 20 in the vicinity of the cavity bottom 26. The induction of the second coil 22 is responsive to the particle accumulation within the cavity 18. The measurements made by energizing the second coil 22 will be indicative of particle accumulation that includes both ferrous and non-ferrous metals in one instance, as well as just non-ferrous metals in another instance. In order to measure just the accumulation of non-ferrous particles within the cavity 18, the electromagnetic coil 24 which is located above the second coil 22 is provided such that, when energized, coil 24 pulls all the ferrous particles out of the lower portion of the cavity 18 in the area of the measuring coil 22, leaving only the non-ferrous particles in such cavity in the vicinity of the coil 22 to be measured.

Figure 2:
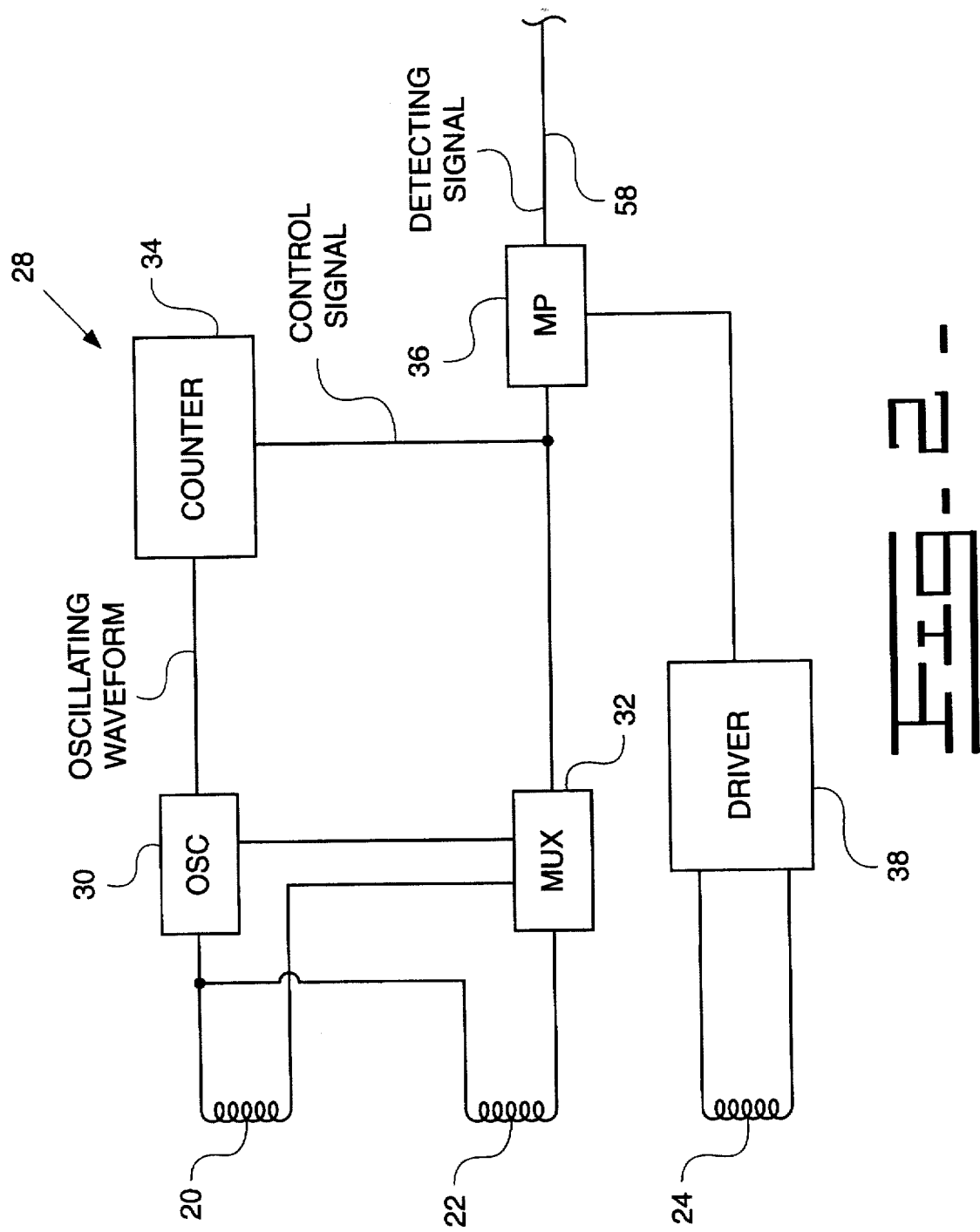
FIG. 2 is a block diagram of the electronic circuitry associated with the present fluid particle sensor device incorporating the principles of the present invention.

Thus, the sensor device 10 is designed to first measure all particle accumulation within the cavity 18 which includes both ferrous and non-ferrous metals, and then measure only the non-ferrous particles by energizing the electromagnetic coil 24 and removing the ferrous particles from the vicinity of the measuring coil 22. The coils 20, 22 and 24 are connected to control circuit 28 as best shown in FIG. 2, which circuit includes the sensing electronics and a microprocessor 36 that calculates the percentage of ferrous and non-ferrous materials in the collection cavity 18. The control circuit 28 may be connected to a monitoring system 60 which may provide a visual warning signal and/or a horn or other audible signal to the operator in the operator compartment of the work machine being monitored, and/or such circuit may be connected to a remote CPU that stores trend and historical data on the maintenance of the work machine.

Referring to FIG. 2, there is shown a block diagram of the control circuit 28 for the present sensor device 10. Control circuit 28 is somewhat similar to the control circuit disclosed in U.S. Pat. No. 5,502,378 and assigned to the assignee of the present application, and the operation of such circuit will now be described with more particularity. The sensing electronic circuit 28 is comprised of an oscillator 30 provided to energize both the first and second coils 20 and 22. The oscillator 30 includes a timer that energizes the coils 20 and 22 with an oscillating waveform. A multiplexer 32 is provided to allow only one coil to be energized at a given time. Consequently, the frequency of the oscillating waveform will be directly related to the inductance of the coil energized. A counter 34 is provided to tally the number of pulses associated with the oscillating waveform. For example, the oscillator 30 will energize one coil, while the counter 34 tallies the number of pulses of the oscillating waveform associated with the one coil. Once the number of pulses reaches a predetermined number, the counter 34 resets. Responsively, the multiplexer 32 causes the other coil to energize and counter 34 tallies the numbers of pulses of the oscillating wave associated with such other coil.

The counter 34 additionally produces control signals. The control signals are continuous pulse width modulated signals wherein the duration of the high pulse level is responsive to one coil being energized, for example, coil 22, while the low pulse level is responsive to the other coil 20 being energized. The control signals are delivered to the microprocessor 36 which produces a detecting signal 58 having a duty cycle that is responsive to the duty cycle of the control signals in order to provide greater resolution. The electromagnetic coil 24 is connected to the microprocessor 36 by means of a driver circuit 38 in a manner which will be hereinafter described.

When a metallic particle enters the collection cavity 18, the energized coil 22, in accordance with well known principles, introduces eddy currents into the particle. The eddy currents are a function, among other properties, of material conductivity. Thus, when a metallic particle enters the cavity 18, eddy currents in the particle cause the effective inductance of the measuring coil 22 to decrease. Consequently, the oscillator 30 will produce the oscillating waveform with an increased frequency. Because eddy currents are a function of material conductivity, the greater the size of a particle or the greater the amount of particle accumulation within the cavity 18, the greater the change in the oscillating waveform frequency. Since eddy current principles apply to both ferrous and non-ferrous metallic particles, the change in frequency of the oscillating waveform is due to the eddy current inductive effects on both the ferrous and non-ferrous particles. In this regard, the frequency range of the measuring coil 22 can be selected such that it will detect both ferrous and non-ferrous metallic particles. It is recognized that the circuit shown in FIG. 2 is exemplary, and the manner of design and construction of this circuit, or a similar circuit, would be commonly known to a person skilled in the art.

Referring to FIG. 3, a flow chart 40 illustrates the operation of the sensor device 10. At predetermined time periods, the sensor 10 first energizes the reference coil 20 at step 42 to determine the temperature of the fluid to establish a base line for the detection of any metallic particles contained within collection cavity 18. Once this baseline is established, coil 22 is energized by the multiplexer 32 at step 44. A measurement of coil 22 is then taken of all of the particles in the cavity 18, which measurement is in the form of a signal generated by coil 22 and such signal is representative of both ferrous and non-ferrous particles. This measurement is stored by the microprocessor 36. Microprocessor 36 then energizes the electromagnetic coil 24 at step 46 by means of the driver circuit 38 and, at this point in time, all of the ferrous particles contained within the bottom 26 of cavity 18 are pulled away from the measuring coil 22 and into the area of the electromagnetic coil 24. A second measurement of coil 22 is now taken at step 48, which measurement or generated signal is now representative of the non-ferrous particles remaining at the bottom 26 of the cavity 18 in the vicinity of measuring coil 22. This second measurement is likewise stored by the microprocessor 36 and the electromagnetic coil 24 is thereafter de-energized at step 50.

Since the first measurement taken from coil 22 at step 44 is representative of the total amount of ferrous and non-ferrous particle accumulation in the collection cavity 18, and since the second measurement taken from coil 22 at step 48 is representative of only the non-ferrous particle accumulation in the collection cavity 18, the microprocessor 36 at steps 52 and 54 can now calculate both the percentage of non-ferrous particles in the cavity 18 as well as the percentage of ferrous particles in the cavity 18. This data or information is then provided in a detecting signal 58 as shown in FIG. 2 and outputted at step 56 of flow chart 40 to either an electronic monitoring system 60 or some other type of warning system for trend and/or component failure analysis. For example, a warning signal may be provided in response to the detecting signal 58 having a duty cycle greater than a predetermined value which will activate some type of visual and/or audio warning signal in the operator compartment of the work machine when the predetermined value is exceeded. In addition, the microprocessor 36 is also able to determine the rate of particle accumulation and this trend data may be stored and accessed by a service tool of a type well known in the art for downloading diagnostic and prognostic information. Similarly, this trend data may be sent to a remote location via an RF communication link known in the art. As a result, microprocessor 36 receives control signals; it determines the amount of both ferrous and non-ferrous particle accumulation in the collection cavity 18; and it produces a detecting signal having a pulse width modulated waveform.

Industrial Applicability

In operation, the present invention or sensor device 10 is used to filter out debris from a lubricating fluid such as hydraulic fluid, engine oil, or any other type of lubricating fluid and thereafter detect the accumulation of both ferrous and non-ferrous particles within such lubricating fluid. When placed in a fluid line, the sensor device 10 is particularly well suited to detect metal particles within the lubricating fluid associated with various systems and components on a particular work machine, for example, within the machine's transmission system, the engine oil system, the hydraulic system, or the final drive system. For example, the present sensor system could be located in a case drain line of a hydraulic pump or motor. As components such as hydraulic pumps and motors wear, tiny particles of ferrous and non-ferrous material such as iron, copper, brass and steel become suspended in the fluid. If one of the components in the particular fluid system becomes excessively worn out and/or is about to fail, the amount of particles suspended in the fluid increases substantially. Likewise, the amount of particles in the collection cavity 18 will increase substantially.

The present sensor device 10 is designed to determine the total amount of metallic particles within the collection cavity 18 and thereafter calculate the percentage of both ferrous and non-ferrous particles with the collection cavity at any particular point in time, which information may be used in diagnosing or predicting a component or system failure. For example, trend data can be stored in the microprocessor and/or transmitted to the operator compartment or to a remote location for use as needed.

Although there has been illustrated and described a specific structure and a specific method of operation, it is clearly understood that the same is merely for purposes of illustration and that changes and modifications may be readily made to both the construction and method of operation of the sensor device 10 by those skilled in the art without departing from the spirit and scope of the present invention.

Other aspects, objects and advantages of the present invention can be obtained from a study of the drawings, the disclosure and the appended claims.

What is claimed is:

1. An apparatus for detecting particles within a fluid comprising:

a housing adapted for coupling onto a fluid line, said housing including a cavity for collecting particles suspended within the fluid;

a first coil wound about the housing, said first coil disposed to generate an electrical signal responsive to the temperature of the fluid, said signal being independent of any particle accumulation within the cavity;

a second coil wound about the collection cavity and disposed to generate electrical signals responsive to the particle accumulation within the collection cavity, said electrical signals being representative of particle accumulation within the collection cavity in response to the change of the inductance of said second coil due to the accumulation of both ferrous and non-ferrous particles within the collection cavity;

an electromagnetic coil wound about the collection cavity to attract ferrous particles into the proximity thereof, the ferrous particles within the collection cavity being pulled away from the second coil when the electromagnetic coil is energized; and a microprocessor coupled with the first, second, and electromagnetic coils and adapted to receive the electrical signals from said first and second coils and to energize the electromagnetic coil, said microprocessor operable to determine the particle accumulation within the collection cavity and to calculate the amount of ferrous particles and the amount of non-ferrous particles within the collection cavity.

2. The apparatus, as set forth in claim 1, further comprising an oscillator selectively coupled with the first and second coils for producing an oscillating waveform, wherein the frequency of the oscillating waveform is a function of the induction of one of said first and second coils.

3. The apparatus, as set forth in claim 2, further comprising a multiplexer adapted to select one coil to energize at a given time.

4. The apparatus, as set forth in claim 3, wherein the oscillator produces an oscillating waveform having a series of pulses the frequency of which is a function of the one energized coil inductance.

5. An apparatus, as set forth in claim 1, wherein said housing includes a screen adapted to catch particles suspended in the fluid for accumulation within said collection cavity.

6. The apparatus, as set forth in claim 1, wherein said microprocessor is operable to produce a detecting signal having a pulse width modulated waveform indicative of the particle accumulation in the collection cavity.

7. The apparatus, as set forth in claim 6, further comprising a monitoring system adapted to receive the detecting signal and produce a warning signal in response thereto if the detecting signal duty cycle exceeds a predetermined value.

8. A method for detecting ferrous and non-ferrous particles within a fluid comprising:
   trapping particles suspended in the fluid within a collection cavity;
   generating a signal indicative of the ferrous and non-ferrous particle accumulation within a particle measuring area of the collection cavity;
   removing the ferrous particles from the vicinity of the particle measuring area of the collection cavity;
   generating a signal indicative of the non-ferrous particle accumulation within the particle measuring area of the collection cavity.

9. The method, as set forth in claim 8, including the further step of outputting a detecting signal from said microprocessor indicative of the ferrous and non-ferrous particle accumulation within said collection cavity.

10. A method for detecting ferrous and non-ferrous particles within a fluid comprising:
   providing an apparatus adaptable for connection to a fluid line, said apparatus including first and second coils, an electromagnetic coil, and a collection cavity for holding ferrous and non-ferrous particles, said collection cavity having a particle measuring area associated therewith, the inductance of the second coil being responsive to the ferrous and non-ferrous particle accumulation within the particle measuring area;
   trapping particles passing through said fluid line within the collection cavity;
   energizing the first coil and generating a signal indicative of the temperature of the fluid passing through said apparatus;
   energizing the second coil and generating a signal indicative of the total ferrous and non-ferrous particle accumulation within the particle measuring area of said collection cavity;
   energizing the electromagnetic coil to attract ferrous particles away from the particle measuring area of the collection cavity;
   energizing the second coil and generating a signal indicative of the non-ferrous particle accumulation within the particle measuring area of the collection cavity;
   providing a microprocessor coupled with said first and second coils and with said electromagnetic coil adapted to receive the signals generated from said first and second coils, said microprocessor determining the percentage of ferrous particles within said collection cavity and determining the percentage of non-ferrous particles within said collection cavity; and
   outputting a detecting signal indicative of the ferrous and non-ferrous particle accumulation within said collection cavity.

11. The method, as set forth in claim 10, further comprising:
   providing a monitoring system for receiving the outputted detecting signal indicative of the ferrous and non-ferrous particle accumulation within the collection cavity; and
   producing a signal responsive to the detecting signal if said signal exceeds a predetermined value.

12. The apparatus of claim 1 wherein the amount of ferrous particles comprises a percentage and the amount of non-ferrous particles comprises a percentage.

13. The method of claim 8, further comprising providing an apparatus having a collection cavity therewithin, said apparatus being adapted for insertion into a fluid line and being capable of generating electrical signals, said collection cavity having the particle measuring area.

14. The method of claim 8, further comprising providing a microprocessor coupled with said apparatus for calculating the percentage of ferrous and non-ferrous particles within said collection cavity, said microprocessor being adapted to receive the generated signals respectively indicative of the ferrous and non-ferrous particle accumulation within the measuring area.

15. The method of claim 8, further comprising
   determining the percentage of ferrous particles within the collection cavity; and
   determining the percentage of non-ferrous particles within the collection cavity.

* * * * *